Jan. 21, 1964 A. MEILLAND Plant Pat. 2,348
ROSE PLANT
Filed Feb. 5, 1963
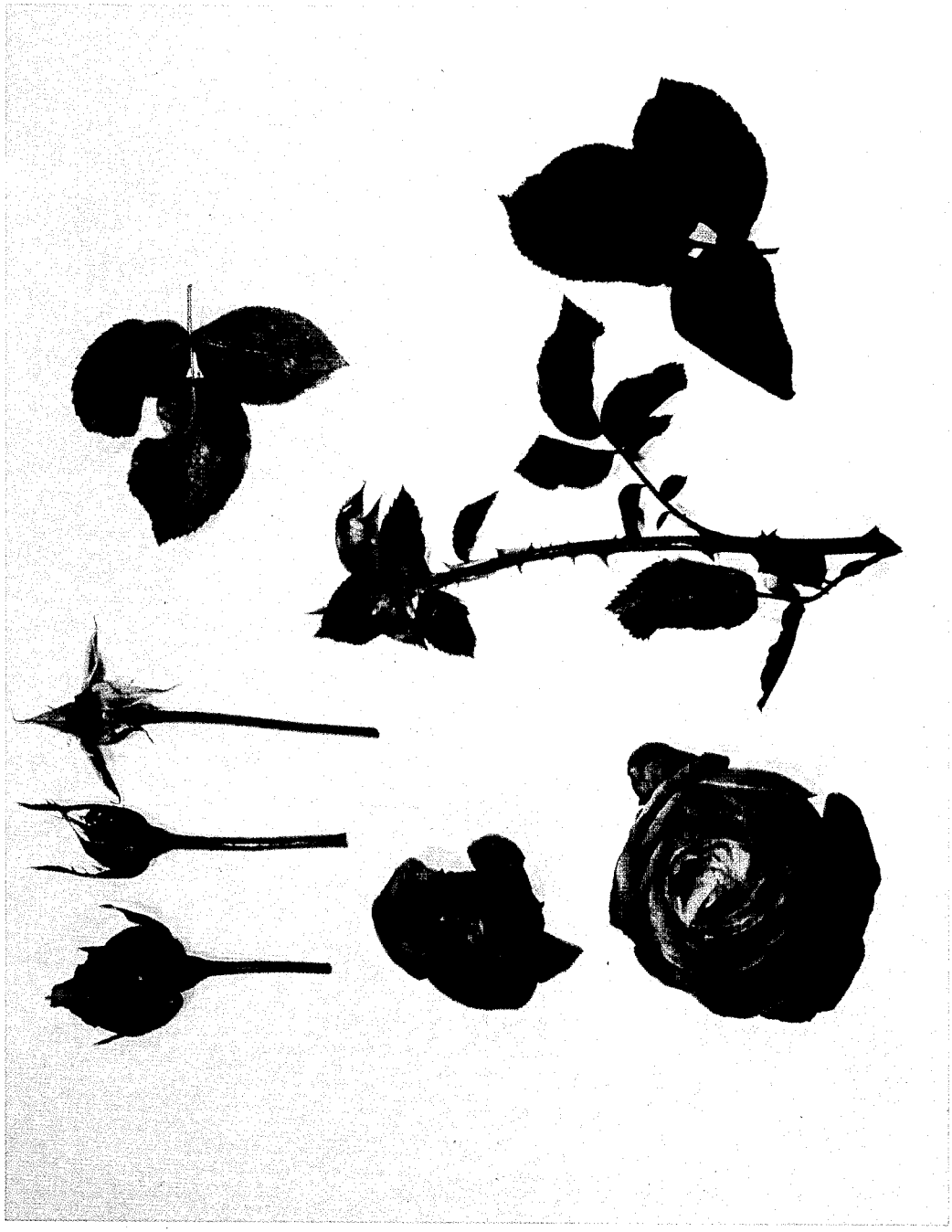
Inventor.
Alain Meilland
By: Robb & Robb
Attorneys.

United States Patent Office

Plant Pat. 2,348

Patented Jan. 21, 1964

2,348

ROSE PLANT

Alain Meilland, Alpes Maritimes, France, assignor to The Conard-Pyle Company, West Grove, Pa., a corporation of Pennsylvania Filed Feb. 5, 1963, Ser. No. 256,485

1 Claim. (Cl. Plt.—21)

The present invention relates to a new and distinct variety of rose plant of the hybrid tea class, which was originated by me by crossing an unnamed and unpatented seedling derived from a cross of "Happiness" (U.S. Plant Patent No. 911), known in France as "Rouge Meilland," × "Independence" (U.S. Plant Patent No. 1,036), known in Germany as "Kordes' Sondermeldung," with the variety "Peace" (U.S. Plant Patent No. 591), known in France as "Mme. A. Meilland."

The primary objective of this breeding was to obtain a new rose variety of good vigor and growth, similar to the variety "Peace," but which bears flowers of red general color tonality. This objective was fully achieved, along with other desirable features, as evidenced by the following unique combination of characteristics which are outstanding in the new variety and which distinguish it from its parents, as well as from all other varieties of which I am aware:

(1) A vigorous and upright habit of growth;

(2) Attractive Dark Green and leathery foliage;

(3) Large, double and high-centered blooms having moderate fragrance; and (4) A distinctive and attractive Tyrian Purple general color tonality of the flowers.

As compared with the variety "Peace," the new variety has the same characteristics in respect to foliage, vigor and habit, but has a distinct difference in color tonality of the flowers, combined with moderately strong fragrance.

In comparison with the unnamed seedling parent, the new variety has a superior growth habit, while the general color tonality of the flowers is Tyrian Purple in contrast with the lighter orange tinted general coloration of the flowers of this parent.

Asexual reproduction of the new variety by budding, as performed in France, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

Th following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid tea.

Breeding: Seedling.

*Seed parent.*—An unnamed seedling of "Happiness" × "Independence."

*Pollen parent.*—"Peace."

Propagation: Holds its distinguishing characteristics through succeeding propagations by budding.

*Flower*

Locality where grown and observed: West Grove, Pennsylvania, U.S.A.

Flowers borne: Generally singly to stem; on strong stems of from medium to long length.

Quantity of bloom: Abundant, outdoors.

Continuity: Continuous.

Fragrance: Moderate.

*Nature.*—Tea.

Bud:

*Peduncle.*—Medium length; medium heavy; erect; stiff; rough; with medium number of light Reddish Brown hairs. Color—Lettuce Green, Plate 861/2.

*Before calyx breaks.* — Size — medium. Form — medium length; ovoid; with a conspicuous neck; with foliaceous appendages on the surface of the bud; with bristle-like foliaceous parts extending beyond the tip of the bud equal to ¼ or more of its length.

*As calyx breaks.*—Color—Ruby Red, Plate 827.

*As first petal opens.*—Size—medium. Form—ovoid. Color—outside: Chrysanthemum Crimson, Plate 824/2, blotched with Ruby Red, Plate 827; inside: near Tyrian Purple, Plate 727, but with luminescent effect, and with base of petal and point of attachment Aureolin, Plate 3.

*Opening.*—Opens up well.

Bloom:

*Size (when fully open).*—Large; from 4 inches to 4½ inches.

*Petalage.*—Double; from 46 to 54 petals; arranged regularly.

*Form.*—High-centered at first, but becoming cupped; petals being at first loosely rolled outward, and remaining rolled outward at maturity.

Petals:

*Texture.*—Leathery.

*Appearance.*—Inside—satiny. Outside—shiny.

*Shape.*—Outer petals—roundly obovate. Intermediate petals—roundly obovate. Inner petals—roundly obovate.

This description of a newly opened flower was made from a rose grown outdoors during the month of September at West Grove, Pennsylvania, U.S.A.:

*Color.*—Outer petal—outside surface: Spiraea Red, Plate 025/1, occasionally blotched with Tyrian Purple, Plate 727, and with point of attachment Primrose Yellow, Plate 601/2; inside surface: Tyrian Purple, Plate 727, grading to Tyrian Purple, Plate 727/1 over basal ¼, with point of attachment Primrose Yellow, Plate 601/1. Intermediate petal—outside surface: near Spiraea Red, Plate 025/1, with point of attachment Primrose Yellow, Plate 601/1; inside surface: near Tyrian Purple, Plate 727 where exposed to sunlight, with masked area of petal Tyrian Purple, Plate 727/2, and with point of attachment Primrose Yellow, Plate 601/2 bordered by Persian Rose, Plate 628/3. Inner petal—outside surface: near Spiraea Red, Plate 025/1, with point of attachment Primrose Yellow, Plate 601/1, and often with a streak of Rose Pink, Plate 427/2 extending along the midrib; inside surface: Tyrian Purple, Plate 727 where exposed to sunlight, with masked area of petal Tyrian Purple, Plate 727/2, and with point of attachment Primrose Yellow, Plate 601/2 bordered by Persian Rose, Plate 628/3.

This description was made from a rose that was open for three days outdoors during the month of September at West Grove, Pennsylvania, U.S.A.:

*Color.*—Outer petal—outside surface: Spiraea Red, Plate 025/1, with point of attachment Primrose Yellow, Plate 601/2; inside surface: Tyrian Purple, Plate 727 over upper half of petal, grading to Tyrian Purple, Plate 727/1 and then to Tyrian Purple, Plate 727/2 at base, with point of attachment Primrose Yellow, Plate 601/2. Inner petal—outside surface: near Spiraea Red, Plate 025/1, with point of attachment Primrose Yellow, Plate 601/2; inside surface: near Tyrian Purple, Plate 727, grading to Tyrian Purple, Plate 727/1, with point of attachment Primrose Yellow, Plate 601/2.

*General color effect.*—Newly opened flower—near Tyrian Purple, Plate 727. Three days open—near Tyrian Purple, Plate 727.

*Behavior.*—Drop off cleanly.

*Flower longevity.*—On bush in garden—4 days in September. Cut roses grown outdoors and kept at living room temperatures—4 days in September.

*Reproductive Organs*

Stamens: Many; arranged regularly about pistils.

Filaments: Most with anthers; medium length.

*Color.*—Primrose Yellow, Plate 601/29/63 at base, grading to Neyron Rose, Plate 623/3.

Anthers: Open at various times; medium size; occasionally an anther fused with a petaloid.

*Color.*—Lemon Yellow, Plate 4.

Pollen: Moderate abundance.

*Color.*—Gold.

Pistils: Medium number.

Styles: Uneven; medium length; medium heaviness; bunched.

Stigma:

*Color.*—Yellow.

Ovaries: All enclosed in receptacle.

Hips: None observed.

Sepals: Permanent; moderately long; spear-shaped.

Seeds: None observed.

*Plant*

Foliage:

*Leaves.*—Compound of 3 or 5 leaflets; normal abundance; moderately large; leathery.

*Leaflets.*—Shape—oval, with apex acute. Base—obtuse. Margin—simply serrate.

*Color.*—Mature—upper surface: slightly darker than Spinach Green, Plate 0960; under surface: near Spinach Green, Plate 0960/3. Young—upper surface: near Fern Green, Plate 0862, overlaid with Garnet Brown, Plate 00918/3; under surface: Oxblood Red, Plate 00823, with midrib Fern Green, Plate 0862/1, grading to Oxblood Red, Plate 00823 at apex.

*Rachis (the supporting stem of the compound leaf).*—Medium size. Upper side—grooved; hairy. Under side—sparsely prickly.

*Stipules.*—Moderately long; medium width; with moderately short points turning out at an angle of 45°.

*Disease resistance.*—Comparable to that of the average variety grown under the same cultural conditions at West Grove, Pennsylvania, U.S.A.

Growth:

*Habit.*—Upright; much-branched.

*Growth.*—Free.

*Canes.*—Moderately heavy.

*Main stems.*—Dull. Color—Spinach Green, Plate 0960/1. Prickles—several; color: Fern Green, Plate 0862. Hairs—few; color: near Fern Green, Plate 0862.

*Branches.*—Dull. Color—Spinach Green, Plate 0960/1. Prickles—several; color: near Fern Green, Plate 0862, lightly overlaid with Oxblood Red, Plate 00823/3. Hairs—none.

*New shoots.*—Dull. Color—Fern Green, Plate 0862/1, overlaid on side exposed to sun with Garnet Brown, Plate 00918/2. Prickles—several; color: near Garnet Brown, Plate 00918/2. Hairs—none.

I claim:

A new and distinct variety of rose plant of the hybrid tea class, substantially as herein shown and described, characterized particularly as to novelty by the unique combination of a vigorous and upright habit of growth, attractive Dark Green and leathery foliage, large, double and high-centered blooms which have moderate fragrance, and a distinctive and attractive Tyrian Purple general color tonality of the flowers.

No references cited.